(12) United States Patent
Pollock et al.

(10) Patent No.: US 8,704,178 B1
(45) Date of Patent: Apr. 22, 2014

(54) CONTAINER FOR SURGICAL OBJECT AND FLUID MONITORING SYSTEM

(71) Applicant: Surgitrac Corporation, Boca Raton, FL (US)

(72) Inventors: Richard A. Pollock, Atlanta, GA (US); Mahmood S. Kassam, Ontario (CA); Thomas D. Cox, Grand Prairie, TX (US)

(73) Assignee: Surgitrac Corporation, Boca Raton, FL (US)

( * ) Notice: Subject to any disclaimer, the term of this patent is extended or adjusted under 35 U.S.C. 154(b) by 0 days.

(21) Appl. No.: 13/839,450

(22) Filed: Mar. 15, 2013

(51) Int. Cl.
*G01J 1/00* (2006.01)
*A61B 19/02* (2006.01)

(52) U.S. Cl.
CPC .................. *A61B 19/0287* (2013.01)
USPC ....................................... 250/336.1

(58) Field of Classification Search
CPC ........... A61B 19/0271; A61B 19/0287; A61B 19/029
USPC ........................................... 250/336.1–336.2
See application file for complete search history.

(56) References Cited

U.S. PATENT DOCUMENTS

| | | |
|---|---|---|
| 3,367,431 A | 2/1968 | Baker |
| 3,613,899 A | 10/1971 | Schleicher et al. |
| 4,295,537 A | 10/1981 | McAvinn et al. |
| 4,361,231 A | 11/1982 | Patience |
| 4,419,232 A * | 12/1983 | Arntyr et al. .................. 210/164 |
| 4,422,548 A | 12/1983 | Cheesman et al. |
| 4,478,332 A | 10/1984 | Wiestmiller |
| 4,903,837 A | 2/1990 | Duello |
| 4,922,922 A | 5/1990 | Pollock et al. |
| 5,009,275 A | 4/1991 | Sheehan |
| 5,031,642 A | 7/1991 | Nosek |
| 5,033,703 A * | 7/1991 | Allen, Sr. ........................ 248/97 |
| 5,258,742 A | 11/1993 | Soldevila Domingo et al. |
| 5,443,082 A | 8/1995 | Mewburn |

(Continued)

FOREIGN PATENT DOCUMENTS

| | | |
|---|---|---|
| WO | 2011075433 | 6/2011 |
| WO | 2011156671 | 12/2011 |
| WO | 2012078500 | 6/2012 |

OTHER PUBLICATIONS

O'Connor, Anahad, "When Surgeons Leave Objects Behind", New York Times, pp. 1-4, Sep. 24, 2012.

*Primary Examiner* — Kiho Kim
(74) *Attorney, Agent, or Firm* — Fleit Gibbons Gutman Bongini & Bianco PL; Jose Gutman (57) ABSTRACT

A container, system, method, and computer readable storage medium, for monitoring at least one of surgical object and fluid placed into the container are provided. The container includes a rigid top member including at least one port opening therein, having a recessed portion of the underside of the top member along an outer perimeter, a rigid retaining ring sized and shaped to match the size and shape of the recessed portion along the outer perimeter, and a flexible bag body having an open top portion and a sealed bottom portion, an outer perimeter of the open top portion being folded over the rigid retaining ring, the rigid retaining ring with the folded over perimeter of the open top portion of the flexible bag body being mated and locked in the recessed portion of the underside of the rigid top member along the outer perimeter in a fluid-tight seal arrangement.

20 Claims, 6 Drawing Sheets

(56) References Cited

U.S. PATENT DOCUMENTS

| | | | |
|---|---|---|---|
| 5,629,498 A | 5/1997 | Pollock et al. | |
| 5,641,947 A | 6/1997 | Riddle, Jr. | |
| 5,650,596 A | 7/1997 | Morris et al. | |
| 5,664,582 A | 9/1997 | Szymaitis | |
| 5,836,553 A * | 11/1998 | Bergaila | 248/99 |
| 5,889,530 A | 3/1999 | Findlay | |
| 5,918,197 A | 6/1999 | Toussant et al. | |
| 5,923,001 A | 7/1999 | Morris et al. | |
| 5,931,824 A | 8/1999 | Stewart et al. | |
| 6,026,818 A | 2/2000 | Blair et al. | |
| 6,302,461 B1 | 10/2001 | Debras et al. | |
| 6,777,623 B2 | 8/2004 | Ballard | |
| 6,777,625 B2 | 8/2004 | Oldendorf | |
| 6,781,067 B2 | 8/2004 | Montagnino et al. | |
| 6,900,396 B2 | 5/2005 | Murdter | |
| 6,998,541 B2 | 2/2006 | Morris et al. | |
| 7,001,366 B2 | 2/2006 | Ballard | |
| 7,019,650 B2 | 3/2006 | Volpi et al. | |
| 7,297,834 B1 | 11/2007 | Shapiro | |
| D557,421 S | 12/2007 | Fleck et al. | |
| D568,186 S | 5/2008 | Blair et al. | |
| 7,378,604 B2 | 5/2008 | Truong | |
| 7,378,694 B2 | 5/2008 | Yi et al. | |
| 7,378,904 B2 | 5/2008 | Risbo | |
| 7,411,506 B2 | 8/2008 | Volpi et al. | |
| 7,469,727 B2 | 12/2008 | Marshall | |
| 7,501,948 B2 | 3/2009 | Roemerman et al. | |
| 7,512,583 B2 | 3/2009 | Benson et al. | |
| 7,526,455 B2 | 4/2009 | Benson et al. | |
| 7,541,933 B2 | 6/2009 | Volpi et al. | |
| 7,557,711 B2 | 7/2009 | Volpi et al. | |
| D603,048 S | 10/2009 | Fleck et al. | |
| 7,609,159 B2 | 10/2009 | Benson et al. | |
| 7,656,286 B2 | 2/2010 | Benson et al. | |
| D611,610 S | 3/2010 | Fleck et al. | |
| 7,671,744 B2 | 3/2010 | Volpi et al. | |
| 7,696,877 B2 | 4/2010 | Barnes et al. | |
| 7,703,674 B2 | 4/2010 | Stewart et al. | |
| 7,755,491 B2 | 7/2010 | Volpi et al. | |
| 7,760,097 B2 | 7/2010 | Volpi et al. | |
| 7,764,178 B2 | 7/2010 | Volpi et al. | |
| 7,784,468 B2 | 8/2010 | Fabian et al. | |
| D624,531 S | 9/2010 | Fleck et al. | |
| 7,795,491 B2 | 9/2010 | Stewart et al. | |
| 7,893,840 B2 | 2/2011 | Volpi et al. | |
| 7,898,420 B2 | 3/2011 | Blair et al. | |
| 8,063,760 B2 | 11/2011 | Volpi et al. | |
| 8,105,296 B2 | 1/2012 | Morris et al. | |
| 8,111,162 B2 | 2/2012 | Barnes et al. | |
| 8,174,366 B2 | 5/2012 | Volpi et al. | |
| 8,181,860 B2 | 5/2012 | Fleck et al. | |
| 8,256,674 B2 | 9/2012 | Fleck et al. | |
| 2003/0062221 A1 * | 4/2003 | Burrow et al. | 184/1.5 |
| 2006/0151059 A1 * | 7/2006 | Ours et al. | 141/314 |
| 2007/0285249 A1 | 12/2007 | Blair et al. | |
| 2008/0204245 A1 | 8/2008 | Blair et al. | |
| 2010/0033309 A1 | 2/2010 | Blair | |
| 2010/0108079 A1 | 5/2010 | Blair | |
| 2010/0109848 A1 | 5/2010 | Blair et al. | |
| 2011/0004276 A1 | 1/2011 | Blair et al. | |
| 2011/0163854 A1 * | 7/2011 | Hamelin et al. | 340/10.1 |
| 2011/0181394 A1 | 7/2011 | Blair | |

* cited by examiner

CONTAINER FOR SURGICAL OBJECT AND FLUID MONITORING SYSTEM

CROSS-REFERENCE TO RELATED APPLICATION

This application is related to co-pending U.S. patent application Ser. No. 13/839,042, filed on even date herewith; the entire disclosure being herein incorporated by reference in its entirety.

FIELD OF THE DISCLOSURE

The present disclosure generally relates to surgical object monitoring systems, and more particularly to a container for use with surgical object (e.g., a surgical sponge) monitoring system that can monitor and track surgical objects and the fluid of a patient during a surgical procedure.

BACKGROUND

Surgical object monitoring systems have attempted to keep track of surgical objects with varying degrees of success. Some monitoring systems have relied almost entirely on manual counting of objects, such as sponges, while being used in a surgical operating room. This manual tracking process can be particularly error prone, which can result in unfortunate cases of surgical objects remaining inside patients after a surgical operation. Some monitoring systems have attempted to utilize complex and expensive technical solutions utilizing objects modified with RFID devices and/or barcodes to be scanned before, during, and after surgical procedures. These conventional monitoring systems continue to experience problems in attempting to keep track, and possibly locate lost objects such as sponges, that remain inside a patient. These conventional monitoring systems also fail to monitor fluids, such as blood, serum, or other fluids, that can be lost by a patient during a surgical procedure.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

As required, detailed embodiments are disclosed herein; however, it is to be understood that the disclosed embodiments are merely examples and that the devices, systems and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, commanded, altered, modified, built, composed, constructed, designed, or that has any combination of these characteristics to carry out a given function. The term "adapted to" describes hardware, software or a combination of hardware and software that is capable of, able to accommodate, to make, or that is suitable to carry out a given function.

The terms "controller", "computer", "server", "client", "computer system", "computing system", "personal computing system", or "processing system" describe examples of a suitably configured processing system adapted to implement one or more embodiments of the present disclosure. Any suitably configured processing system is similarly able to be used by embodiments of the present disclosure. A processing system may include one or more processing systems or processors. A processing system can be realized in a centralized fashion in one processing system or in a distributed fashion where different elements are spread across several interconnected processing systems.

The terms "computing system", "computer system", and "personal computing system", describe a processing system that includes a user interface and which is suitably configured and adapted to implement one or more embodiments of the present disclosure. The terms "network", "computer network", "computing network", and "communication network", describe examples of a collection of computers and devices interconnected by communications channels that facilitate communications among users and allows users to share resources. The terms "wireless network", "wireless communication network", and "wireless communication system", similarly describe a network and system that communicatively couples computers and devices primarily or entirely by wireless communication media. The terms "wired network" and "wired communication network" similarly describe a network that communicatively couples computers and devices primarily or entirely by wired communication media.

Figure 1:
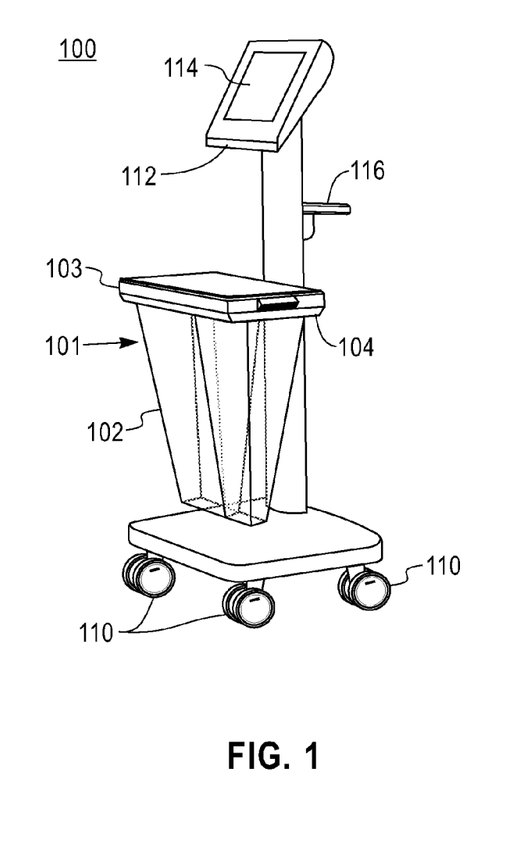
FIGS. 1 to 5 are perspective views of an example of a monitoring system for use during a surgical procedure, according to the present disclosure.

Referring to FIG. 1, an example of a surgical object and fluid monitoring system (Monitor System) 100 is shown, according to various embodiments of the present disclosure.

The Monitor System 100 supports a container 101 that can receive and contain surgical objects, including but not limited to sponges and fluid-retaining sponges. The container 101, according to various embodiments is disposable. The container 101, according to various embodiments is constructed of lightweight plastic or polymer materials and film. The container 101, according to the present example, includes a container main body 102 that is directly mechanically coupled to a container top 103. According to various embodiments, the container main body 102 and the container top 103 are mechanically coupled in a fluid-tight seal.

The container main body 102, according to the present example, comprises a flexible film bag 102 that can be easily compressed and collapsed into a small volume adjacent to the underside of the container top 103. When the container top 103 is supported in a horizontal orientation, as shown in FIG. 1, the flexible film bag 102 easily falls down from the top 103 (by the force of gravity) thereby fully expanding and conforming to its fully expanded open shape, as shown in FIG. 1. The container main body 102 is therefore self-expanding from its compressed volume shape to its fully expanded ready-to-use shape, by the force of gravity.

In the present example, as illustrated in FIG. 1, the container 101 is supported by its top 103 that is securely supported by an optical sensor ring (OSR) 104 of the Monitor System 100. The OSR 104 is mechanically coupled to, and supported by, a vertical spine 106 of the Monitor System 100. The flexible bag 102 falls down from the supported top 103 by the force of gravity. The empty flexible bag 102, when supported by the OSR 104, fully expands to its open shape ready-to-use with the Monitor System 100.

As shown in the example of FIG. 1, the flexible bag 102 has a tapering shape that tapers from wider cross-section about the top 103 to narrower cross-section towards the bottom of the bag 102. This container 101 is easy to transport and store, especially with the container main body 102 compressed/collapsed to a reduced volume shape adjacent to the underside of the top 103.

Figure 3:
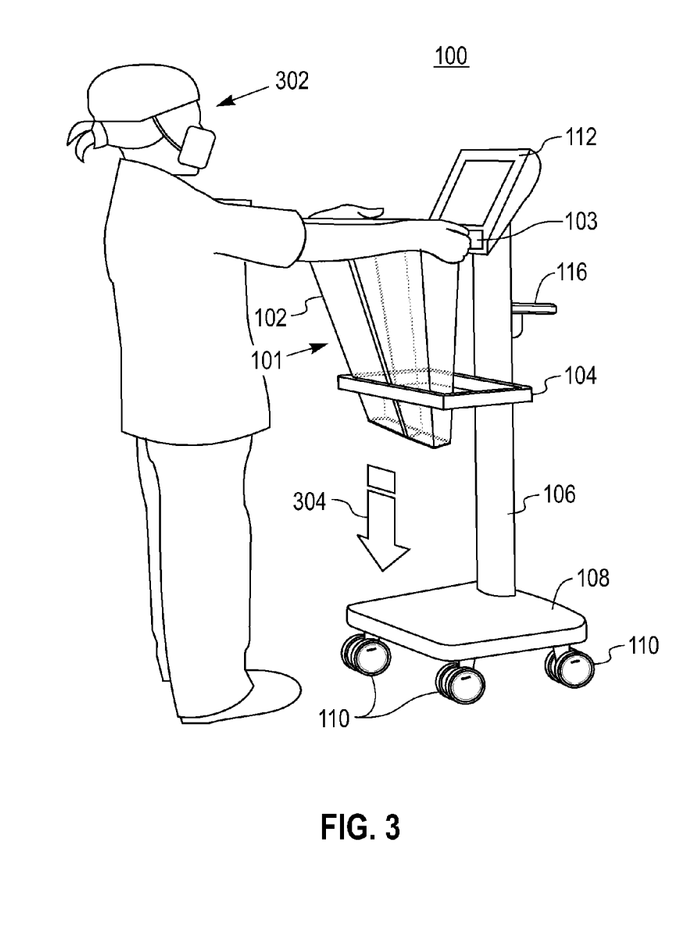

For example, the empty, compressed, container 101 can be easily stored in a sealed storage package (not shown) that keeps the container 101 sanitary and ready to use in a clean room such as a surgical operating room. Then, when a user (e.g., a surgical nurse or assistant) opens the sealed storage package and removes therefrom the container 101, by only holding the top 103 by its handles (as shown in FIG. 3), the container self-expands to its full ready-to-use shape by the force of gravity. The user does not have to manipulate the container main body 102 to cause the container 101 to fully expand to its full open shape ready to use. The user can support the container top 103 in a horizontal orientation (e.g., by holding the top 103 by its handles in a natural gesture similar to carrying a tray) and the empty container main body 102 will self-expand (e.g., fully expand to its open ready-to-use shape). This container 101 design provides a user friendly container product that is easy to store and transport, easy to extract out of the OSR for disposal of the container and its content, and easy to dispose of after use.

Figure 2:
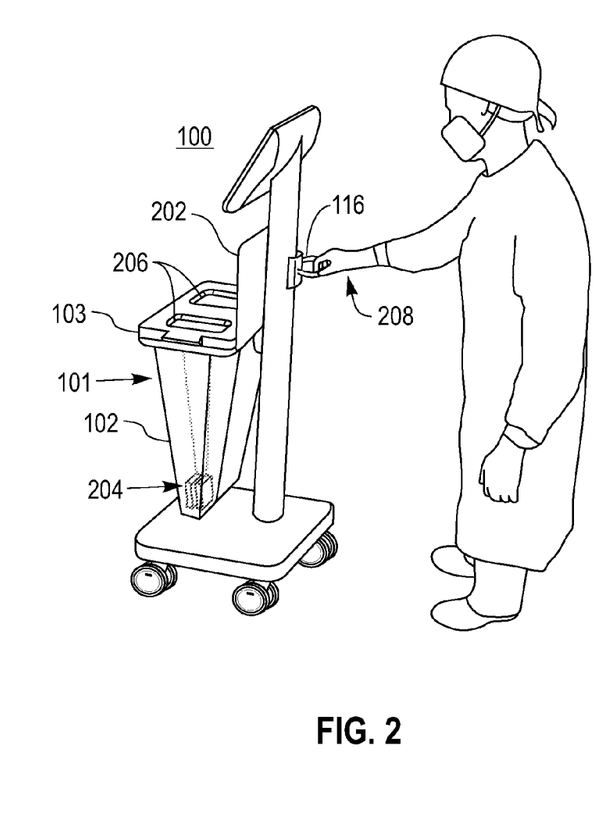

As shown in FIG. 1, the Monitor System 100 comprises a vertical spine 106 that is maintained in a substantially vertical orientation and supported by a base 108 of the Monitor System 100. The base 108 may include, according to various embodiments, several wheels 110 that allow the user to easily move (i.e., push-pull) the Monitor System 100 to a desired location for use. A handle 116 extends from the vertical spine 106 such that a user of the Monitor System 100, for example, can grab the handle 116 and thereby pull or push the Monitor System 100 on its wheels 110 to a desired location. FIG. 2 shows a user with a hand 208 grabbing the handle 116 of the Monitor System 100.

As shown in FIG. 1, the Monitor System 100 includes controller unit 112 that is supported at the top of the vertical spine 106. The controller unit 112, according to the present example, includes a touch screen liquid crystal display 114 that provides a user interface for a user of the Monitor System 100. Any type of touch screen display technology may be used in the Monitor System 100, as may be desired for various applications.

With reference to FIG. 2, the Monitor System 100 is shown with the container 101 having received an object, such as a fluid filled sponge, 204 within an internal compartment of the container 101. The container main body 102 can include one or more compartments that each can receive and contain objects, such as fluid filled sponges, that are dropped into the container 101 through one or more ports or openings 206 at the top 103 of the container 101.

A top lid 202 may be used to cover the one or more openings 206 on the container top 103 after the container has received one or more objects 204 and its use has been completed. The top lid 202 will cover the one or more openings 206 and, according to certain embodiments, will create a fluid-tight seal with the container top 103. This facilitates removal of the container 101 from the Monitor System 100 as well as disposal of the container 101. The container 101 with the top lid 202 covering the one or more openings 206, and optionally creating a fluid-tight seal at the container top 103, securely contains the object 204 in a compartment inside the container 101. With the object 204, such as a fluid-filled sponge, being securely contained and sealed within the container 101, the container 101 can be easily removed from the Monitor System 100 and disposed accordingly without concern for leakage of bio-contaminated and/or hazardous objects or fluids from the container 101.

As shown in FIG. 3, the user 302 can hold the container 101 by the container top 103, such as by handles on either side of the container top 103. The container main body (e.g., a flexible bag) 102 fully expands to its ready-to-use shape and the empty container 101 can easily be lowered 304 by the user 302 onto the optical sensor ring 104 which then acts as support for the container 101. The arrow 304 indicates how the user 302 lowers the container 101 into the center opening of the optical sensor ring 104. Of course, the reverse procedure can be used to remove the container 101 from the OSR 104. By lifting the container 101, e.g., a used container 101 containing one or more objects 204, the user 302 can remove the container 101 from the OSR 104 and from the Monitor System 100. The user can then be safely and conveniently dispose of the removed container 101.

It should be noted that while the optical sensor ring 104 is shown as a continuous rigid ring structure in the present example, according to other embodiments the optical sensor ring 104 could have a hinged portion (not shown) that is rotatable away from the other portions of the OSR 104. For example, a left portion or a right portion of the OSR 104 could be the hinged rotatable portion. The hinged rotatable portion could be secured (e.g., using a locking or latching device) to the remaining structure of the OSR 104 to form the continuous ring shape of the OSR 104. When a container 101 is full of objects 204, and its total weight may be significant, the user 302 could avoid having to lift the full container 101 from the OSR 104. By opening the locking or latching device at the hinged rotatable portion, the user can hold the handles at the top 103 of the full container 101 and remove it from the OSR 104 by lateral movement—to the left or right of the OSR 104. The user 302 would not have to lift the full container 101 higher than its current level while supported by the OSR 104.

Figure 4:
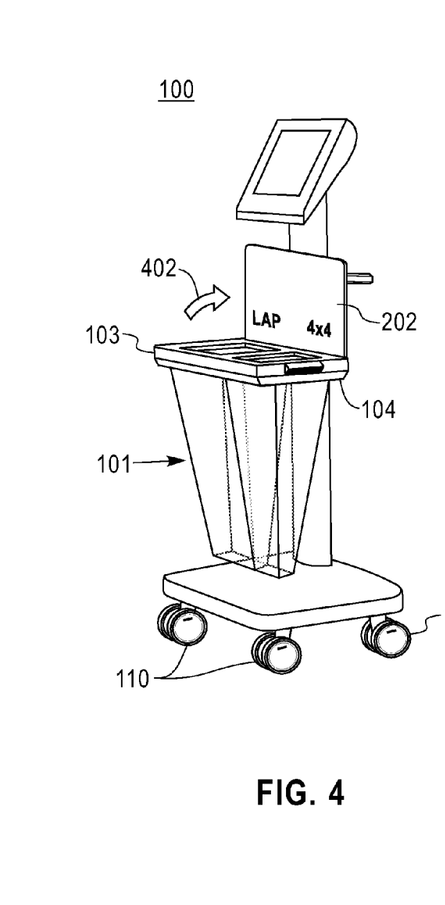

As shown in FIG. 4, after the container 101 is placed through the center opening of, and supported by, the OSR 104, the top lid 202, according to one example, can be rotated up-and-to-the-rear of the container top 103, as indicated by the arrow 402. According to certain embodiments, the top lid 202 then remains vertically supported by the vertical spine 106, as shown in FIG. 4. Optionally, a small magnet may be embedded in the top lid 202. When the top lid 202 is resting vertically against the vertical spine 106 the top lid 202 is removably secured to the vertical spine 106 by magnetic force between the small magnet in the top lid 202 and a metallic surface of the vertical spine 106. A user can, as necessary, pull and remove the top lid 202 from the vertical spine 106 and rotate the lid 202 back onto the top surface of the container top 103.

The top lid 202 provides a splash guard for any fluids that may be splashed by fluid-containing objects being placed into the container 101 through the one or more openings 206. Additionally, the container lid 202 can include writing or symbols, as illustrated in FIG. 4, to visually help guide the user to locate the appropriate opening 206 to drop an object into the container 101. As shown in FIG. 4, there are two compartments within the container 101. One compartment holds smaller objects (e.g. small fluid-containing sponges), while the second opening 206 is for a second compartment in the container 101 that holds larger objects (e.g. large fluid-containing sponges). In this way, according to the present example, the container 101 can be used to not only contain objects 204, but also to help sort these objects in the corresponding compartments. The objects 204 are sorted by attributes of each group of objects such as by size, thickness, or other dimensions, of sponges being used in a surgical procedure. According to various embodiments, other attributes of objects 204 can be used for sorting the objects 204 in the different compartments within the container 101.

Figure 5:
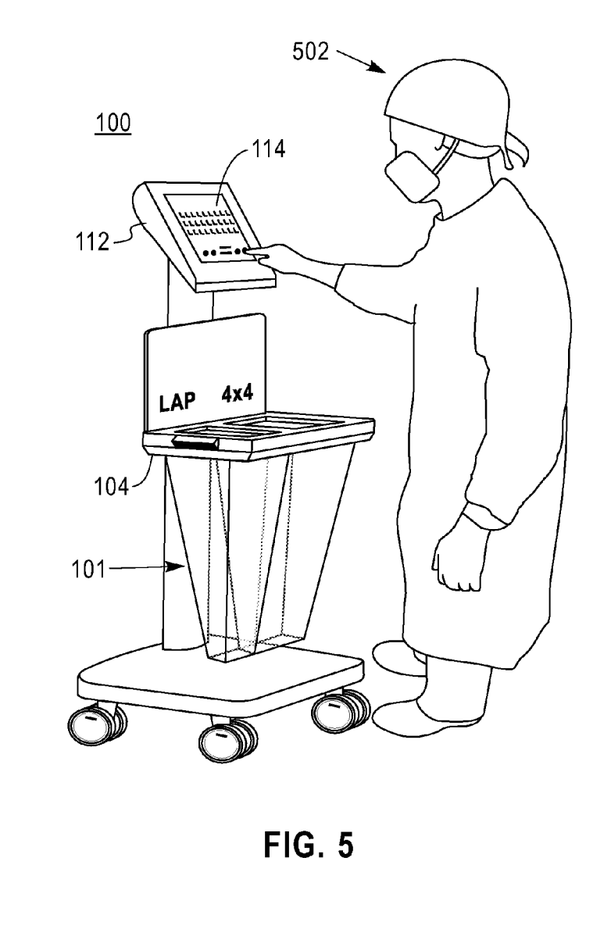

Referring to FIG. 5, the user 502 can touch the touch screen 114 of the Monitor System 100 to communicate information with the Monitor System 100. For example, the user 502 can use a finger of the hand, or a stylus, to touch locations on the touch sensitive surface of the touch screen 114. In this way, the user 502 can communicate commands and/or data to the Monitor System 100, and optionally configure parameters of the Monitor System 100, in accordance with a particular implementation of the Monitor System 100.

The user 502 can enter configuration information into the Monitor System 100 to let the Monitor System 100 know, for example, how many compartments are in the container 101 and the types of objects and their attributes that may be expected to be placed in these compartments. Additionally, the user 502 can provide information to the Monitor System 100 to inform the Monitor System 100 of how many objects to expect to be placed in each of the compartments in the container 101.

The touch screen 114 provides a user interface that not only receives information from the user 502, but also displays information to the user. In this way, the user 502 can be informed of certain events that occur with the Monitor System 100 and certain conditions experienced by the Monitor System 100. For example, the touch screen display 114 can display a count of the number of objects, such as fluid-filled sponges, that have been deposited in each of the compartments in the container 101. Additionally, for example, the touch screen display 114 can display to the user 502 the approximate amount of fluid by weight (or by calculated volume) that has been accumulated in the compartments of the container 101.

Once the Monitor System 100 has been configured and is ready to use, the user places each object (e.g., such as a fluid-filled sponge removed from a patient during a surgical procedure) at one of the one or more openings 206 in the top 103 of the container 101, and then allows the object to drop through the particular opening 206 and down into a receiving compartment within the container main body 102.

Each of the one or more openings 206, according to the present example, comprises a funnel shape with a gradual inward sloping surface from the top surface of the container top 103 down toward the inside of a compartment in the container main body 102. This funnel shape helps guide the objects being placed at the opening 206 into the particular compartment of the container 101. Also, this funnel shape more reliably places the falling object at a generally central region of the opening 206. By dropping the object 204 down from a central region of the opening 206, a plurality of sensors in the OSR 104 just below the opening 206 can more reliably sense/detect the falling object, as will be discussed below.

One or more sets of optical emitters located along an inner surface of the OSR 104 emit respective one or more optical beams (e.g., infrared "IR" beams) across a central opening of the OSR 104 aimed at respective one or more optical sensors located along an opposing inner surface of the OSR 104. For example, a first group of alternating optical emitters and optical sensors may be located along an inner surface of a rear portion of the OSR 104.

Additionally, a second group of alternating optical sensors and optical emitters (opposing the first group of optical emitters and sensors) may be located along an inner surface of a front portion of the OSR 104. Each optical emitter is matched to an opposing optical sensor to create an optical beam that traverses across the center opening of the OSR 104.

A detection region is formed by a plurality of optical beams spanning across the front portion and rear portion of the center opening of the OSR 104. The detection region is just below the end of each funnel shaped port or opening 206 in the container 101.

To facilitate the optical beams traversing across the center opening of the OSR 104 while the container 101 is supported on the OSR 104, according to various embodiments, the construction and material of the walls of the container main body 102, at least in the detection region just below the funnel shaped opening(s) 206, are optically transparent over the relevant wavelength and frequency range of the Infra-Red (IR) optical beam, e.g., over IR wavelength and frequency range of the optical beam sensed by the sensor.

Optionally, the material and construction of the walls of the container main body 102, at least in the detection region just below the funnel shaped opening(s) 206, can be optically transmissive or optically transflective, at the relevant wavelength and frequency range of the optical beam. This material and construction is designed to enhance the ability of each of the optical beams emitted from an emitter device at the inner surface about the ring center opening of one portion of the OSR 104 to reach and be detectable by the matching sensor device at the opposing inner surface about the ring center opening of another portion of the OSR 104.

For example, according certain embodiments, Dupont Corporation makes a clear polyethylene film product called CLEAR that provides optical qualities suitable for use in the construction and material of the walls of the container main body 102, at least in the detection region just below the funnel shaped opening(s) 206. Another desired aspect of the construction of the walls of the container 101, at least in the detection region just below the funnel shaped opening(s) 206, is that the walls traversed by an optical beam be oriented substantially perpendicular to the axis of the optical beam. This perpendicular wall orientation relative to the optical beam axis enhances the amount of optical energy that passes through the wall and thereby enhances the ability of the beam to reach and be detectable by the corresponding optical sensor device.

Therefore, in view of the discussion above, an object (e.g., a sponge) placed at the opening 206 while dropping into the corresponding compartment in the container 101 will have to pass through the detection region covered by the one or more optical beams (e.g., IR beams). The one or more beams traverse across this detection region such that when each object is dropped into an opening 206 of the container 101 at least one beam is broken by the falling object while the object passes the detection region. The break of the beam is sensed by the respective optical sensor and a beam break signal is sent from the optical sensor to a processor/controller in the Monitor System 100, to indicate that an object has been dropped into the particular port opening 206.

A more sophisticated approach to sensing and monitoring an object being dropped through a detection region is provided here according to various embodiments. A plurality of beams (time and spatially multiplexed), between the inner surface of the rear portion of the OSR 104 and the inner surface of the front portion of the OSR 104, are spaced apart a known distance from each other in the detection region. After at least one beam break is detected by the processor/controller the sensors and the processor/controller can continuously monitor the beam break(s) while the object continues to fall past the detection region. The beam-break-sense monitoring, for example, can be repeated every 10 milliseconds until all of the optical beams are sensed again (i.e., no beam breaks detected). The spatial location of the beam break(s) would signify the specific port (i.e., opening 206) at the top of the container through which an object enters.

Key objectives of various embodiments include, but are not limited to, reliably sorting the object types (in this example two different sponge types correspond to two respective openings 206, i.e., two ports, at the top of the container); providing a valid count of the appropriate object type thrown in the container (eliminating/minimizing false positives); and estimating the fluid content in each such object.

The sorting of object type, according to the present example, is done by providing two ports on top of the container, each port identified with a specific sponge type (this has been described somewhat elsewhere in the present disclosure). Each port is blanketed by a set of IR beams (see, for example, FIG. 14), and each set of IR beams is multiplexed, scanned and monitored by the processor/controller. The processor/controller can then identify the sponge type that was dropped based on which port the IR beam(s) was interrupted.

In order to achieve a reliable object (e.g. a used sponge) count (and eliminate false positives), the key is in the use of an "intelligent" algorithm that uses information from the sensor beam breaks and the incremental weight change measurement (such as using a load cell that will be more fully described below) when a sponge (or object) is thrown in the container through one of the ports. Namely, with general reference to FIGS. 14, 15, and 16, of related co-pending U.S. patent application Ser. No. 13/839,042, filed on even date herewith, the entire disclosure being herein incorporated by reference, when an object passes through the beams 1402, 1404, a beam first "breaks" and then "unbreaks" at the tail-end of the passage of the object. The object will fall to the bottom of the container within a maximum time, ΔTdmax 1512, and an incremental weight change, ΔW 1610 will be measured at ΔTW 1606 (ΔTdmax 1512 plus a Delta $T_s$ 1604, i.e., plus a noise signal settling time) relative to the baseline reference weight established at TBB 1508—when the beam "unbreaks" after a "break"). So, a valid count is recorded only if ΔW 1610 is valid and it is within the pre-stored weight range of fluid content (i.e., between zero to fully saturated sponge weight). The following three exceptions should be noted, however.

First, if the beam is broken (e.g., by inserting one's fingers through port or sponge stuck at the port), no count will be registered because either the beam is broken and no weight change — or — the beam is continuously broken with or without weight change. Either case would violate the rules for a valid count, as has been described above.

Secondly, if the beam is broken properly (with the "break" and "unbreak" sequence in place) but the incremental weight ΔW 1610 is outside the prescribed range, the count is considered invalid.

Third, if a foreign weight is placed on the container (e.g. tray, tongs, etc.), the temporary or permanent increase of the overall weight of the container due to the foreign weight will not hamper the measurement of the actual incremental weight ΔW 1610 of a sponge (object) that has traversed the optical sensors; hence the sponge will be counted as valid. Note that ΔW 1610 is a relative measurement as shown in FIG. 16.

Once a valid sponge (object) is detected in the container and counted based on the above rules, then for each ΔW 1610 measured the incremental fluid content of the container is calculated by subtracting from ΔW 1610 the pre-stored dry weight (Wdry) of the sponge type. This incremental fluid content is accumulated to the running total Fluid count maintained by the Monitor.

The fluid content of the object extracted/calculated from its incremental weight ΔW 1610 is used to accumulate the total fluid count. Hence, any extraneous weight placed on the container (or removed via evaporation of fluid from the container) would not, and should not, factor into the accumulated total fluid count maintained by the Monitor.

Now, continuing with the description of the example Monitor System 100, and with particular reference to FIGS. 4 and 5, a plurality of optical emitter beams blanket the region just below the one or more openings 206 at the top 103 of the container 101. The one or more optical emitter beams pass from a first inner side of the OSR 104, through the opposing walls of the container main body 102, and across to and below the one or more funnel openings 206, to one or more optical sensors located in an opposing second inner side of the OSR 104. The one or more optical beams, therefore, traverse the ring center opening from across opposing inner sides of the container main body 102 just below the funnel shaped openings 206 of the container top 103. The optical beams, according to various embodiments, pass through the walls of the container main body 102, at least about the detection region where the optical beams traverse the ring center opening of the OSR 104 from across opposing inner sides of the container main body 102.

After the Monitor System 100 detects that an object has been dropped into the compartment within the container 101, e.g. by detecting one or more beams between optical emitters and optical sensors have been broken, the Monitor System 100 can additionally monitor the incremental weight change due to the object that has been dropped in the container 101.

After an object is dropped into the compartment of the container 101, the object after traversing one or more of the optical beams in the detection region of the container 101, will further drop and make contact either 1) with the bottom of the container main body 102 (corresponding to an empty compartment of the container 101), or 2) with the object(s) already resting on the bottom. When the object drops inside a compartment of the container 101 and delivers its incremental weight to the container 101, such as when the object reaches the bottom of the container 101, the object's weight can be established by the Monitor System 100.

According to certain embodiments, the Monitor System 100 includes an electronic load cell mechanically coupled to the OSR 104 that supports the container 101, and thereby senses the weight of the container 101 and its contents. Thus, the load cell can provide a signal that indicates the incremental weight of the object that has been dropped into the container 101, as the weight is transferred from the container 101 to the OSR 104, and thereby transferred to the electronic load cell in the Monitor System 100. In this way, the Monitor System 100 detects an object being dropped into the container 101 and establishes the incremental weight of the object that was just dropped in the container 101.

Based on information in the Monitor System 100, such as information that the user 502 configured in the Monitor System 100 by using the touch screen display 114, the attributes of the object expected to be dropped into a particular compartment in the container 101 are known to the Monitor System 100. In the case where the object 204 in the container 101 is carrying fluid, the additional weight of the fluid in the object 204 will also be part of the total weight of the dropped object that is detected by the load cell and the Monitor System 100. By subtracting the known approximate weight of the object 204 before being filled with fluid from the total weight of the dropped object 204 (e.g., which is fluid filled) the Monitor System 100 can establish the weight of the fluid in the object that was dropped into the container 101.

This incremental weight of fluid can additionally indicate a certain volume of fluid when the type of fluid is known. For example, for blood filled sponges that are dropped into the container 101 the Monitor System 100 calculates, based on the cumulative measured weight of the blood contained in the sponges, the approximate amount of total volume of blood removed (via the sponges) from the patient during a surgical procedure. That is, the weight of the blood carried in the sponges can be used to approximate the cumulative volume of the blood loss.

By information being displayed to the user via the touch screen display 114, for example, the Monitor System 100 can inform the user of the total count of objects being dropped in the container 101, the type of objects sorted in a compartment in the container 101, and an estimation of the total volume of fluid loss (e.g., blood loss) from a patient during surgical procedure. That is, according to various embodiments, the volume estimate would be based on the weight of the fluid carried within the objects being deposited into the container 101. One or more controllers (or processors) in the Monitor System 100 can be used to monitor the objects being dropped in the container 101 and then calculate and display via the touch screen display 114 valuable information to the user, such as the count of the total number of objects being dropped into the container 101, sorted by type of object that is dropped into the container 101, and a calculated estimate of fluid loss volume from a patient as indicated by the weight of the fluid in the fluid-filled objects 204 being dropped into the container 101.

Figure 6:
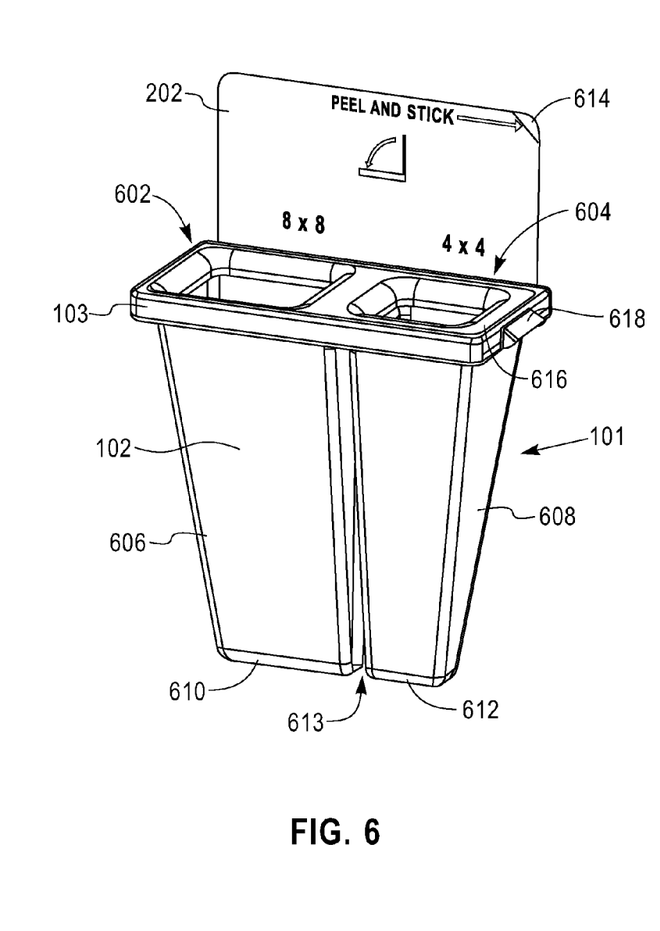
FIG. 6 is a front perspective view of an example of a container suitable for us in a monitoring system, according to the present disclosure.

With reference to FIGS. 6 to 11, a more detailed discussion of an example container 101 suitable for use with the Monitor System 100 is provided below. As shown in FIG. 6, the container 101 is shown fully assembled and ready to use. The container 101 includes a container main body 102 and a container top 103. The container top 103 includes, according to the present example, two openings 602, 604. These openings 602, 604, according to the example, are funnel shaped as shown in FIG. 6. The first opening 602 corresponds to a first inner compartment 606 in the container main body 102. The second opening 604 corresponds to a second compartment 608 in the container main body 102. The first compartment 606 is separated from the second compartment 608 by a container gap opening 613, as shown in FIG. 6.

Each compartment 606, 608, has a bottom 610, 612, respectively. Each bottom portion 610, 612, of the container main body 102 is constructed with additional container body material making the bottoms 610, 612 thicker than the other walls of the container main body 102. This thicker bottom material 610, 612, helps facilitate the container main body to fully expand to its empty ready to use shape. The container main body 102, before use, may be provided in a compressed state just below the top 103. This reduced volume is advantageous for storing and shipping the container 101. After removal of a container 101 from a protective packaging by supporting the container 101 from the top, such as by a user holding the handles 618, 802, the container main body 102 due to the added container material at the bottom 610, 612 of the container main body 102 through the force of gravity encourages the container main body 102 to fully expand to its empty ready to use shape as shown in FIG. 6. That is, the container 101, in the example shown in FIG. 6, is self-expanding to its full ready to use shape when supported by the top 103.

The top 103, according to the present example, includes a flat top surface 616 around the two openings 602, 604. A lid 202 can be located on this top surface 616 to cover the openings 602, 604. According to one embodiment, the lid 202 includes a retaining means 614 such as an adhesive surface that when contacting the flat top surface 616 will create an adhesive bond and retain the lid 202 secured on top of the top 103, thereby covering the openings 602, 604 to prevent objects in the compartments 606, 608 from spilling out of the container 101.

According to one embodiment, the lid 202 is secured along one edge of the lid 202 to an edge of the top surface 616 allowing the lid 202 to be rotated from an open position away from the top surface 616 to a closed position where the lid 202 makes contact with the top surface 616, thereby covering the openings 602, 604 in the top 103. The adhesive 614 may be exposed by peeling a film cover from the adhesive surface 614 allowing the adhesive then to bond to the top surface 616 when the lid 202 is rotated on top of the top surface 616.

According to certain embodiments, the top lid 202 when covering the openings 602, 604 in the top 103 additionally creates a fluid tight seal preventing the fluid from objects contained in the one or more compartments 606, 608 from escaping from the container 102. The container 101 can therefore be disposed of safely without exposing users to hazardous materials contained in the container 101.

Figure 7:
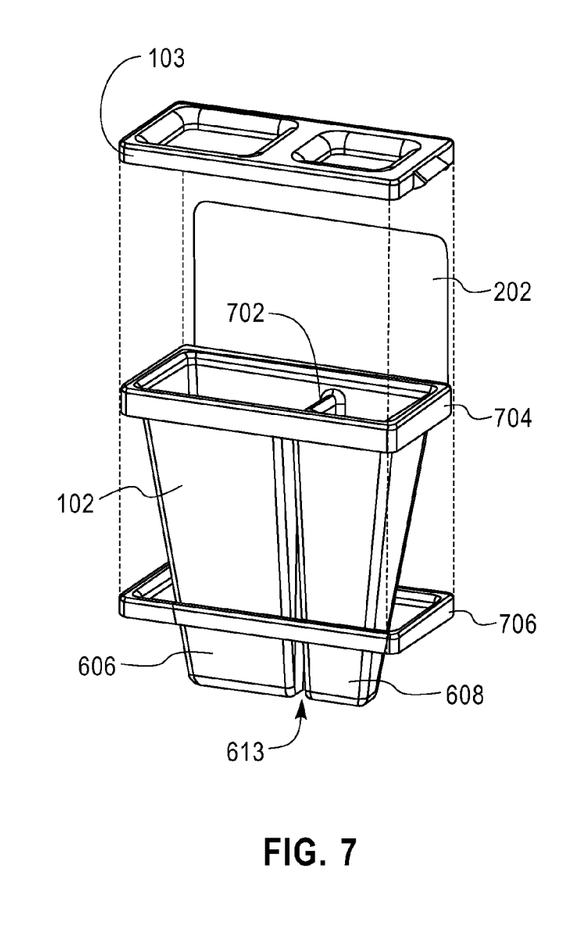
FIG. 7 is a front perspective view of the example container of FIG. 6 partly disassembled to illustrate construction and assembly thereof, according to the present disclosure.

Referring to FIG. 7, the construction and assembly of the container 101 of FIG. 6 is shown. The container main body 102 is held secured to the underside of the top 103 by a retaining ring 706. The four broken lines show the direction of assembly of the container main body 102, the container top 103, and the rigid retaining ring 706.

The container main body includes a fold 704 along the perimeter of the top portion of the container main body 102. The retaining ring 706 is fitted under the fold 704 and then the top 103 is fitted on top of the fold with the rigid retaining ring and the top 103 creating a sandwich with the fold material 704 securing the container main body to the top 103 in a fluid tight seal.

According to the present example, the lid 202 is a rigid or semi-rigid material that is attached to an edge of the container main body 102 allowing the lid 202 to be rotated over the top 103 when the container 101 is fully assembled. As shown in FIG. 7, the two compartments 606, 608, of the container main body 102 are separated by an opened gap 613 between the two compartments 606, 608. The open gap according to the present example, continues up towards the top portion of the container main body 102 until reaching a top fold region 702 extending from a rear surface of the container main body 102 to a front surface of the container main body 102 as shown.

Figure 8:
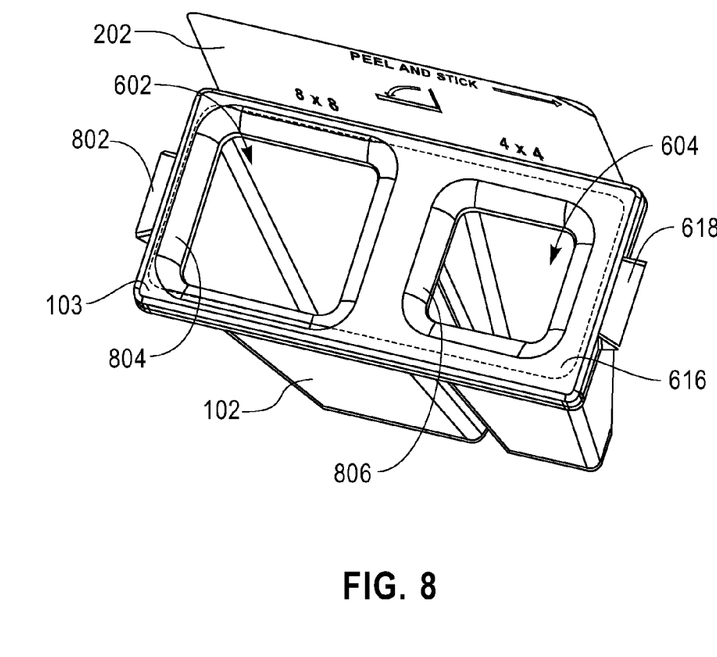
FIG. 8 is a top perspective view of the example container of FIG. 6, according to the present disclosure.

FIG. 8 shows a top perspective view of the container 101 with the lid 202 open away from the top surface 616 of the top 103. The openings 602, 604 are funnel shaped with gradually sloping funnel surface 804, 806, respectively extending downward from the top surface 616 into the respective compartments 606, 608. The gradually inward sloping surface 804 of the first opening 602 and the gradually inward sloping surface 806 of the second opening 604 help guide objects deposited in the respective openings 602, 604 towards a center region of each opening 602, 604 while being deposited in the respective compartments 606, 608. This guiding feature of the surfaces 804, 806 of the openings 602, 604, optimally locates the falling objects in the detection region just below the bottom of the surfaces of 804,806, of the funnel shaped openings 602, 604.

The detection region corresponds to a region across each opening 602, 604, covered by a plurality of optical beams being emitted by optical emitters and sensed by matching optical sensors located along the inner surface of a ring center opening of the OSR 104 of the Monitor System 100. These beams traverse and blanket the openings 602, 604, according to various embodiments, between the rear portion of the container 101 and the front portion of the container 101, while being supported by the top 103 on the OSR 104 of the Monitor System 100.

Because these beams traverse the detection region just below the gradually inward sloping surfaces 804, 806, of the openings 602, 604 of the top 103, each beam, according to the present example, from an optical emitter to its matching optical sensor on the opposing inner surface of the OSR 104 traverses across two container walls of the container main body 102, toward the upper portion of the main container body 102. The material and construction of these container walls is suitable for transmitting these optical beams without significant attenuation of optical energy thereby allowing each beam to reach its matching optical sensor with sufficient energy to be detected.

The walls of the container body 102, at least about the top portion of the main container 102 just below the gradually inwardly sloping surfaces 804, 806, of the openings 602, 604 can be constructed of an optically transmissive material that allows most of the beam energy to transmit and pass through the wall of the container main body 102. For example, a material called CLEAR, which manufactured and distributed by Dupont Corporation, may be suitable for use in construction of the walls of the container main body 102 such that IR beams may transmit substantially unattenuated through these walls of the container main body 102, thereby delivering the beam to the matching optical sensor.

Figure 9:
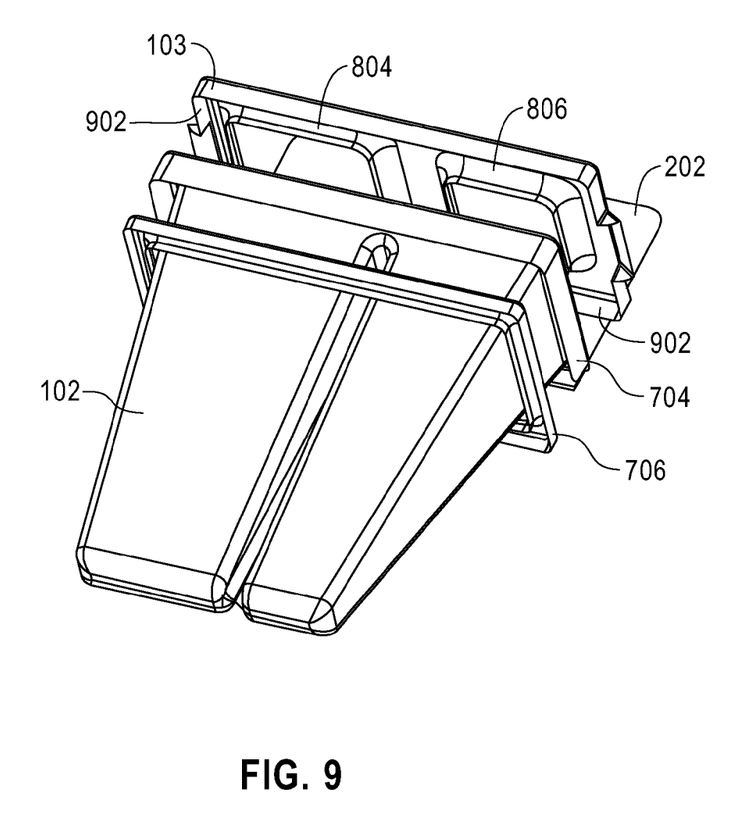
FIG. 9 is a front-bottom perspective view of the example container of FIG. 6, according to the present disclosure.
Figure 10:
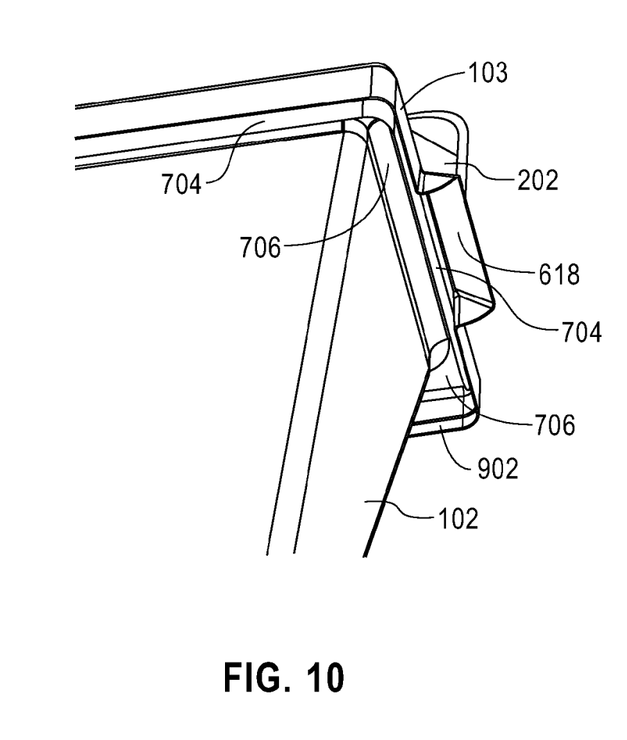
FIG. 10 is a front-bottom perspective view of a portion of the example container of FIG. 6, according to the present disclosure.

FIGS. 9 and 10 show in more detail the construction and arrangement of the underside of the top 103. A rigid retaining ring 706 is shaped to mate into a recessed portion 902 of the underside of the top 103. The fold 704 of the container main body 102 is received in the recessed portion 902 of the underside of the top 103, and is secured therein by the mating of the rigid retaining ring 706 into the recessed portion 902 as shown.

When the rigid retaining ring 706 is passed underneath the fold 704 of the main container body 102, the top 103 at its recessed portion 902 receives the matching rigid retaining ring 706 and the fold 704 into the recessed portion 902. The rigid retaining ring 706 and fold 704 are secured and retained in the recessed portion 902 of the underside of the top 103.

According to various embodiments, the locking arrangement of the rigid retaining ring 706, the fold 704 of the main container body 102, and the recessed portion 902 of the top 103, also creates a fluid tight seal in this region of the container 101. That is, fluid from the objects (e.g., surgical objects, sponges, etc.) contained in the compartments of the container main body 102 will not leak through this sealed region formed by the mating and locking arrangement of the rigid retaining ring 706, the fold 704 of the main container body 102, and the recessed portion 902 of the underside of the top 103.

Figure 11:
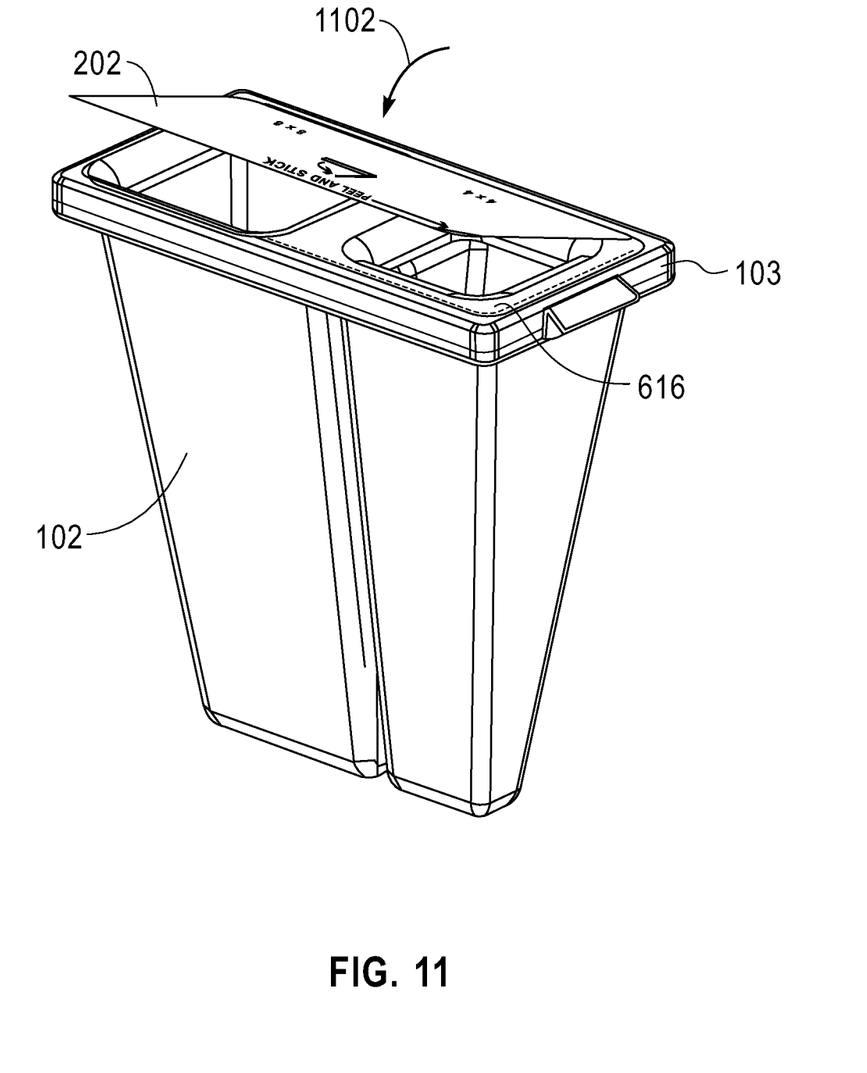
FIG. 11 is a front-right perspective view of the example container of FIG. 6, according to the present disclosure.

Lastly, FIG. 11 illustrates with arrow 1102 how the lid can be rotated 1102 onto the top surface 616 of the top 103. Optionally, a retaining feature or adhesive is located in at least one surface of the top surface 616 of the top 103 and the underside surface of the lid 202.

Information Processing System

The present subject matter can be realized in hardware, software, or a combination of hardware and software. A system can be realized in a centralized fashion in one computer system, or in a distributed fashion where different elements are spread across several interconnected computer systems. Any kind of computer system—or other apparatus adapted for carrying out the methods described herein—is suitable.

The present subject matter can also be embedded in a computer program product, which comprises all the features enabling the implementation of the methods described herein, and which—when loaded in a computer system—is able to carry out these methods. Computer program in the present context means any expression, in any language, code or notation, of a set of instructions intended to cause a system having an information processing capability to perform a particular function either directly or after either or both of the following a) conversion to another language, code or, notation; and b) reproduction in a different material form.

Each computer system may include, inter alia, one or more computers and at least a computer readable medium allowing a computer to read data, instructions, messages or message packets, and other computer readable information from the computer readable medium. The computer readable medium may include computer readable storage medium embodying non-volatile memory, such as read-only memory (ROM), flash memory, disk drive memory, CD-ROM, and other permanent storage. Additionally, a computer medium may include volatile storage such as RAM, buffers, cache memory, and network circuits. Furthermore, in certain embodiments of the computer readable medium, other than a computer readable storage medium as discussed above, the computer readable medium may comprise computer readable information in a transitory state medium such as a network link and/or a network interface, including a wired network or a wireless network, that allow a computer to read such computer readable information.

Non-Limiting Examples

Although specific embodiments of the subject matter have been disclosed, those having ordinary skill in the art will understand that changes can be made to the specific embodiments without departing from the spirit and scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A container having a design and construction for use in a surgical operating room to receive and securely contain fluid-carrying surgical objects in the container, the container comprising:
   a rigid top member including at least one port opening therein, and having a recessed portion of the underside of the top member along an outer perimeter;
   a rigid retaining ring sized and shaped to match the size and shape of the recessed portion of the underside of the top member along an outer perimeter of the rigid top member;
   a flexible bag body having an open top portion and a sealed bottom portion, an outer perimeter of the open top portion being folded over the rigid retaining ring, the rigid retaining ring with the folded over perimeter of the open top portion of the flexible bag body being mated and locked in the recessed portion of the underside of the top member along the outer perimeter of the rigid top member in a fluid-tight seal arrangement; and
   a lid, being rotatably secured along an edge of the lid to an edge of the top surface of the rigid top member in a fluid-tight seal arrangement, that when rotated to a substantially vertical orientation relative to a top surface of the rigid top member providing a splash guard from the fluid-tight seal arrangement of the edge of the lid secured to the edge of the top surface of the rigid top member for any fluids that may be splashed by objects being placed into the container through the at least one port opening.

2. The container of claim 1, wherein the flexible bag body having a tapering shape from the open top portion to the sealed bottom portion, wherein a base of the sealed bottom portion being made with more bag material than the other walls of the tapering shape flexible bag body to provide weight at the base of the flexible bag body when empty and supported by the rigid top member that encourages with gravity a downward expansion of the flexible bag body from a collapsed and compressed shape to a fully expanded shape.

3. The container of claim 1, wherein at least the open top portion of the flexible bag body comprises material that permits IR beam energy from an IR emitter outside the flexible bag body to transmit through the material of the flexible bag body and be detected by a matching IR beam sensor outside of the flexible bag body.

4. The container of claim 1, wherein the open top portion of the flexible bag body just below the at least one port opening of the rigid top member comprises material that permits IR beam energy from an IR emitter outside the flexible bag body to transmit through the material of the flexible bag body and be detected by a matching IR beam sensor outside of the flexible bag body.

5. The container of claim 1, wherein the open top portion of the flexible bag body just below the at least one port opening of the rigid top member comprises optically transmissive material at infrared frequencies compatible with IR beam energy transmitted from an IR beam emitter and detected by a matching IR beam sensor.

6. The container of claim 1, wherein the open top portion of the flexible bag body just below the at least one port opening of the rigid top member comprises optically transmissive film material at infrared frequencies.

7. The container of claim 1, wherein the rigid top member includes handles designed and constructed for a person to hold while carrying the container.

8. The container of claim 1, wherein the rigid top member having a small vertical dimension that cooperates with a compressed and collapsed flexible bag body adjacent to the underside of the rigid top member to provide a small compressed volume shape for the container, and wherein the at least one port opening of the rigid top member comprises a plurality of port openings, and wherein each of the plurality of port openings comprises a funnel shape with a gradual inward sloping surface from a top surface of the rigid top member and within the small vertical dimension of the rigid top member.

9. The container of claim 8, wherein the gradual inward sloping surface of the funnel shape guides objects deposited from the top of the at least one port opening towards a center region of the at least one opening while being deposited into the container.

10. The container of claim 8, wherein the gradual inward sloping surface of the funnel shape being designed within the small vertical dimension to reliably guide objects deposited from the top of each of the plurality of port openings towards a detection region just below and associated with the each port opening of the rigid top member.

11. The container of claim 10, wherein the container design and construction locates the detection region for each port opening of the container to substantially coincide with a detection region of a plurality of IR beams from matched IR emitters and IR sensors in a monitor system that detects surgical objects placed into the container through the each port opening.

12. The container of claim 1, wherein the lid is directly and seamlessly in continuity with an edge of the flexible bag body, and the lid being rotated over the rigid top member during opening or closure of the container.

13. A method with a monitor system and a container for detecting surgical objects being placed into the container, the container comprising a rigid top member including a plurality of port openings therein, and having a recessed portion of the rigid top member along an outer perimeter, a rigid retaining ring sized and shaped to match the size and shape of the recessed portion of the rigid top member along an outer perimeter of the rigid top member, a container body having a flexible bag body having an open top portion and a sealed bottom portion, an outer perimeter of the open top portion being folded over one of the rigid retaining ring and the rigid top member, the rigid retaining ring with the folded over perimeter of the open top portion of the flexible bag body being mated and locked in the recessed portion of the top member along the outer perimeter of the rigid top member in a fluid-tight seal arrangement, and a lid, being rotatably secured along an edge of the lid to an edge of the top surface of the rigid top member in a fluid-tight seal arrangement, and the container body with at least one compartment located below each of the plurality of port openings, the method comprising:
   supporting the container by the rigid top member; and
   rotating the lid and holding it in a substantially vertical orientation relative to the top surface of the rigid top member providing a splash guard from the fluid-tight seal arrangement of the edge of the lid secured to the edge of the top surface of the rigid top member for any fluids that may be splashed by objects being placed into the container through one of the plurality of port openings.

14. The method of claim 13, wherein the container design and construction locates a separate detection region horizontally in the container just below each port opening of the plurality of port openings to substantially coincide with a detection region of a plurality of beams from matched remitters and sensors in a monitor system that detects surgical objects placed into the container through the each port opening of the plurality of port openings, the method further comprising:
    transmitting at least one beam of energy through the container body traversing the detection region located horizontally just below and across one port opening of the plurality of port openings of the rigid top member;
    monitoring at least one sensor to detect at least a beam break followed by a beam make of the at least one beam of energy traversing the detection region in the container; and
    monitoring, based on detection of the beam break followed by the beam make, an incremental weight force of the container due to a surgical object placed into the container through one of the plurality of port openings by:
        measuring a base weight force of the container at the time of the beam break followed by the beam make,
        inhibiting weight force measurement for a predefined time delay which is approximately a calculated time delay of an object falling a distance from a port opening of the container to the sealed bottom of the flexible bag body plus a noise signal settling time, and
        measuring, after the inhibiting, an incremental weight force change of the container by subtracting the base weight force of the container, measured at the time of the beam break followed by the beam make, from a weight force of the container, measured after the predefined time delay while inhibiting weight force measurement.

15. The method of claim 14, further comprising:
    counting valid surgical objects detected placed into each port opening of the container based on detecting a beam break followed by a beam make of the at least one beam of energy traversing the detection region of the each port opening and further followed by detecting a measured incremental weight force change of the container that matches a valid surgical object incremental weight force range associated with the each port opening.

16. The method of claim 14, wherein the method further comprising:
    counting and sorting valid surgical objects detected placed into the container through each of the plurality of port openings.

17. A non-transitory computer readable storage medium, comprising computer instructions which, responsive to being executed by a processor of a monitor system for monitoring at least one of surgical object and fluid placed into a container, the container comprising a to member including a plurality of port openings therein, and a container body having an open top portion and a sealed bottom portion, a separate detection region being located horizontally in the container just below each of the plurality of port openings to substantially coincide with a detection region of a plurality of beams from matched emitters and sensors in a monitor system that detects surgical objects placed into the container through the each port opening, the computer instructions causing the processor to perform operations comprising:
    transmitting at least one beam of energy through the container body traversing a detection region located horizontally just below and across one port opening of the plurality of port openings;
    monitoring at least one sensor to detect at least a beam break followed by a beam make of the at least one beam of energy traversing the detection region of the one port opening; and
    detecting, with a processor, placement of a surgical object into the container through the one of the plurality of port openings with the aid of gravity, based at least on:
        detecting at least a beam break followed by a beam make of the at least one beam of energy traversing the detection region;
        monitoring, based on detection of the beam break followed by the beam make, an incremental weight force of the container due to a surgical object placed into the container through the one port opening of the plurality of port openings by:
            measuring a base weight force of the container at the time of the beam break followed by the beam make,
            inhibiting weight force measurement for a predefined time delay which is approximately a calculated time delay of an object falling a distance from a port opening of the container to the sealed bottom portion of the container body plus a noise signal settling time, and
            measuring, after the inhibiting, an incremental weight force change of the container by subtracting the base weight force of the container, measured at the time of the beam break followed by the beam make, from a weight force of the container, measured after the predefined time delay; and
        determining whether the incremental weight force change of the container matches a predefined incremental weight force range for a valid surgical object corresponding to the one port opening.

18. The non-transitory computer readable storage medium of claim 17, further comprising computer instructions which, responsive to being executed by the processor of the monitor system, cause the processor to perform operations comprising:
    determining, based on determining that a valid surgical object corresponding to the one port opening was located in the one port opening, an incremental fluid content of the container by subtracting a predefined dry weight for the valid surgical object from the incremental weight force change of the container.

19. The non-transitory computer readable storage medium of claim 17, further comprising computer instructions which, responsive to being executed by the processor of the monitor system, cause the processor to perform operations comprising:
    counting, based on determining that a valid surgical object corresponding to the one port opening was located in the one port opening, an increment in a total of surgical objects detected placed into the container through the one port opening.

20. The non-transitory computer readable storage medium of claim 19, further comprising computer instructions which, responsive to being executed by the processor of the monitor system, cause the processor to perform operations comprising:

counting and sorting valid surgical objects detected placed into the container through each of the plurality of port openings.

* * * * *